(12) United States Patent
Mitchell et al.

(10) Patent No.: US 10,596,137 B2
(45) Date of Patent: Mar. 24, 2020

(54) MEDIUM CHAIN FATTY ACIDS AND THEIR TRIGLYCERIDES FOR TREATING ANXIETY

(71) Applicant: NESTEC S.A., Vevey (CH)

(72) Inventors: Ellen Siobhan Mitchell, White Plains, NY (US); Carmen Sandi, Bremblens (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

(21) Appl. No.: 15/551,094

(22) PCT Filed: Feb. 1, 2016

(86) PCT No.: PCT/EP2016/052079
§ 371 (c)(1),
(2) Date: Aug. 15, 2017

(87) PCT Pub. No.: WO2016/131640
PCT Pub. Date: Aug. 25, 2016

(65) Prior Publication Data
US 2018/0028479 A1    Feb. 1, 2018

(30) Foreign Application Priority Data
Feb. 20, 2015   (EP) .................................. 15155852

(51) Int. Cl.
| | | |
|---|---|---|
| *A61K 31/20* | (2006.01) | |
| *A23L 33/12* | (2016.01) | |
| *A23D 9/013* | (2006.01) | |
| *A23K 20/158* | (2016.01) | |
| *A23D 7/01* | (2006.01) | |
| *A23K 50/50* | (2016.01) | |
| *A61K 31/19* | (2006.01) | |
| *A23L 33/00* | (2016.01) | |
| *A61K 9/107* | (2006.01) | |
| *A61K 9/14* | (2006.01) | |
| *A61K 9/16* | (2006.01) | |

(52) U.S. Cl.
CPC .............. *A61K 31/20* (2013.01); *A23D 7/013* (2013.01); *A23D 9/013* (2013.01); *A23K 20/158* (2016.05); *A23K 50/50* (2016.05); *A23L 33/12* (2016.08); *A23L 33/30* (2016.08); *A61K 9/107* (2013.01); *A61K 9/14* (2013.01); *A61K 9/16* (2013.01); *A61K 31/19* (2013.01); *A23V 2002/00* (2013.01)

(58) Field of Classification Search
CPC ........ A61K 31/20; A61K 31/19; A61K 9/107; A61K 9/14; A61K 9/16; A23L 33/12; A23L 33/30; A23D 9/103; A23D 7/013; A23K 20/158; A23K 50/50; A23V 2002/00
See application file for complete search history.

(56) References Cited

PUBLICATIONS

PLoSone 6(6) e20491 (2011).*
Moon et al. Metabolism. Sep. 2014 ; 63(9): 1131-1140.*
Page et al. (Diabetes (2009) 58(5): 1237-1244).*
MedicalNewsToday (2017).*
Mayo Clinic 1998-2018.*
Kavan et al. Am Fam Physician. May 1, 2009;79(9):785-791.*
Linscheer et al. (J. Clinical Investigation; 45(8)1996).*
Nagao et al. (pharmacological Research 61(2010) 208-212).*
Harkins et al. (Medium Chain Triglycerides JAMA. (1968);203(4):272-274).*
Neobee Medium Chain Triglycerides, Stepan Lipid Nutrition, 2012, pp. 1-6.*
International Preliminary Report on Patentability Chapter I.
Written Opinion of the International Search Authority.
International Search Report.
Contreras Carlos M et al: "Anxiolytic-like effects of human amniotic fluid and its fatty acids in Wistar rats.", Behavioural Pharmacology Oct. 2011, vol. 22, No. 7, Oct. 2011 (Oct. 2011), pp. 655-662, ISSN: 1473-5849.
Furukawa S et al: "Antidepressant-like activity of 10-hydroxytrans-2-decenoic acid, a unique unsaturated fatty acid of royal jelly, in stress-inducible depression-like mouse model", Evidence-Based Complementary and Alternative Medicine, Hindawi Publishing Corporation, US, vol. 7, Jan. 1, 2012 (Jan. 1, 2012), pp. 1-6, XP008177130, ISSN: 1741-4288, DOI: 10.1155/2012/139140.
Akihisa Makino et al: "Anxiolytic-like effect of trans-2-decenoic acid ethyl ester in stress-induced anxiety-like model mice", Biomedical Research., vol. 34, No. 5, Jan. 1, 2013 (Jan. 1, 2013), pp. 259-267, XP55205614, JP ISSN: 0388-6107, DOI: 10.2220/biomedres. 34.259.
Japanese Office Action for Patent Appl No. P2017-539441 dated Nov. 13, 2019.

* cited by examiner

*Primary Examiner* — Shirley V Gembeh
(74) *Attorney, Agent, or Firm* — K&L Gates LLP (57) ABSTRACT

The present invention provides a medium chain fatty acid (MCFA) for use in treating and/or preventing anxiety.

4 Claims, 8 Drawing Sheets

MEDIUM CHAIN FATTY ACIDS AND THEIR TRIGLYCERIDES FOR TREATING ANXIETY

CROSS-REFERENCE TO RELATED APPLICATIONS

The present application is the National Stage of International Application No. PCT/EP2016/052079, filed on Feb. 1, 2016 which claims benefit to European Application No. 15155852.5, filed Feb. 20, 2015. The entire contents of the above applications are incorporated by reference as if recited in full herein.

FIELD OF THE INVENTION

The present invention relates to the field of treating anxiety and anxiety disorders.

BACKGROUND TO THE INVENTION

Anxiety is an unpleasant state of inner turmoil, often accompanied by nervous behaviour, such as pacing back and forth, somatic complaints and rumination. It is the subjectively unpleasant feelings of dread over anticipated events and may be described as a feeling of fear, worry and uneasiness, usually generalized and unfocused as an overreaction to a situation that is only subjectively seen as menacing.

There are several recognised types of anxiety disorders, including panic disorder, social anxiety disorder, specific phobias and generalised anxiety disorder. Symptoms vary depending of the type of anxiety disorder, but generally include: feelings of panic, fear and uneasiness; problems sleeping; cold or sweaty hands and/or feet; shortness of breath; heart palpitations; dry mouth; numbness or tingling in the hands or feet; nausea; muscle tension and dizziness.

Anxiety disorders are heterogeneous in nature and are associated with many potential causative mechanisms. Neurotransmitters such as gamma-aminobutyric acid (GABA), serotonin and norepinephrine have been implicated in anxiety and drugs acting upon these receptors are currently in use as anxiolytics. Various neuropeptides, hormones and transcription factors have also been implicated in anxiety development and drugs acting on these targets are also used as therapies.

Anxiety disorders are also commonly treated by psychotherapy, cognitive-behaviour therapy, lifestyle changes and relaxation therapy. Patients suffering from anxiety may be advised to consider modifying their diet. Magnesium deficiency may contribute to anxiety, depression and insomnia, whilst inadequate intake of vitamin B and calcium can exacerbate anxiety symptoms. Other foods or substances which patients suffering from anxiety may be advised to avoid include nicotine, caffeine and stimulant drugs and foods including salt and artificial additives, such as preservatives. Patients may be advised to ensure their daily diet includes foods such as wholegrain cereals, leafy green vegetables and low fat dairy products and to choose fresh, unprocessed foods whenever possible.

There is a need for further approaches to treat and prevent anxiety and anxiety disorders.

SUMMARY OF ASPECTS OF THE INVENTION

The present invention is based on the determination that administration of medium chain triglycerides (MCTs) to a subject can alleviate anxiety.

Thus, in a first aspect the present invention provides a medium chain fatty acid (MCFA) for use in treating and/or preventing anxiety.

The MCFA may be decanoic acid or octanoic acid.

The MCFA may be in the form of a medium chain triglyceride (MCT). Each of the fatty acid moieties of the MCT may comprise the same number of carbons.

In a second aspect the present invention provides a composition comprising a MCFA as defined in the first aspect of the invention for use in treating and/or preventing anxiety.

The composition may comprise decanoic acid and octanoic acid.

The composition may comprise a decanoic acid to octanoic acid ratio of approximately 3:2 wt/wt.

The composition may be in the form of a food stuff. For example, the composition may be in the form of a human food stuff.

The composition may be in the form of a complete nutritional product.

The composition may be in a powdered form. The composition may be in a spray dried form. The composition may be in the form of an oil-in-water emulsion.

The composition may be in the form of a beverage, mayonnaise, margarine, low fat spread, a dairy product, a cheese spread, processed cheese, a dairy dessert, a flavoured milk, cream, a fermented milk product, cheese, butter, a condensed milk product, an ice cream mix, a soya product, pasteurised liquid egg, a bakery product, a confectionary product, confectionary bar, chocolate bar, high fat bar, liquid emulsion, spray dried powder, freeze dried powder, HUT pudding, Pasteurised pudding, gel, jelly, yoghurt or a food with a fat-based or water-containing filling.

The anxiety may be stranger anxiety, social anxiety disorder, generalised anxiety disorder, general anxiety, phobia, panic disorder, obsessive-compulsive disorder or posttraumatic stress disorder.

In a further aspect the present invention relates to the use of a MCFA as defined in the first aspect of the invention in the manufacture of a composition for the treatment and/or prevention of anxiety.

In a further aspect the present invention relates to a method for treating and/or preventing anxiety in a subject comprising administering an effective amount of a MCFA as defined in the first aspect of the invention or a composition as defined in the second aspect of the invention to the subject.

DESCRIPTION OF THE FIGURES

FIG. 6—IRS-1 phosphorylation in striatum homogenate of MCT- vs control-treated rats FIG. 7—Complex I protein expression in rat cortex following a 2 week administration of MCTs FIG. 8—A) Plasma ketone levels following ingestion of MCT8 or MCT10. B) Levels of plasma β-HB and brain β-HB following ingestion of MCT8 or MCT10.

DETAILED DESCRIPTION

Medium Chain Fatty Acid

A medium chain fatty acid (MCFA) refers to a fatty acid composed of 6 to 10, 6 to 11 or 6 to 12 carbon atoms.

In particular embodiments the MCFA may have between 8 and 10 carbon atoms. In particular, the MCFA may be decanoic acid or octanoic acid.

Deconoic acid is also known as capric acid and is a saturated fatty acid of formula $CH_3(CH_2)_8COOH$. It is also referred to herein as C10.

Octanoic acid is also known as caprylic acid and is a saturated fatty acid of formula $CH_3(CH_2)_6COOH$. It is also referred to herein as C8.

The MCFA may be in the form of triglycerides, diacyl-glycerides, monoacyl-glycerides, phospholipids, lyso-phospholipids, cholesterol and glycolipids.

The MCFA may be in the form of a triglyceride. In particular, the MCFA may be in the form of a medium chain triglyceride (MCT). That is, the MCFA may be in the form of a triglyceride in which each of the three fatty acid moieties of the triglyceride is a MCFA.

In particular, the MCFA may be in the form of a MCT in which each of the fatty acid moieties comprises the same number of carbons. For example, the MCT may comprise three decanoic acid moieties or three octanoic acid moieties.

MCTs are present in low amounts in palm oil and coconut oil, for example. Decanoic acid and octanoic acid form around 5 to 8% and 4 to 10% of the fatty acid composition of coconut oil, respectively.

The present inventors have determined that administration of MCTs to a subject increases Insulin receptor substrate-1 (IRS-1) phosphorylation.

IRS-1 is an adaptor protein mediating Insulin-like growth factor (IGF) receptor activation of Akt, via PI3K. Akt acts as a master switch regulator of energy and metabolic processes such as glucose metabolism, apoptosis and proliferation.

Thus, with wishing to be bound by theory, the MCFAs and MCTs may treat and/or prevent anxiety by altering mitochondrial activity, for example by increasing IRS-1 phosphorylation, in particular phosphorylation of serine 312 of IRS-1.

In certain embodiments, the MCFA, MCT or composition is not administered in combination with arginine and/or fish oil.

Composition

In a second aspect the present invention provides a composition comprising a MCFA as defined in the first aspect of the invention for use in treating and/or preventing anxiety.

The composition may comprise a plurality of MCFAs as defined in the first aspect of the present invention. In other words, the composition may comprise fatty acids composed of 6 to 10, 6 to 11 or 6 to 12 carbon atoms.

In particular embodiments, the composition may comprise MCFAs composed of 8 to 10 carbon atoms.

The composition may be in a form suitable for delivering a dosage of at least about 5 g/l to 150 g/l decanoic acid per day. The dosage may be about 5 g/l, 10 g/l, 15 g/l, 20 g/l, 30 g/l, 40 g/l, 50 g/l, 60 g/l, 70 g/l, 80 g/l, 90 g/l, 100 g/l, 110 g/l, 120 g/l, 130 g/l, 140 g/l, 150 g/l, 175 g/l, 200 g/l, 225 g/l, 250 g/l or 500 g/decanoic acid per day.

The composition may be in a form suitable for delivering a dosage of at least about 5 g/l to 150 g/l octanoic acid per day. The dosage may be about 5 g/l, 10 g/l, 15 g/l, 20 g/l, 30 g/l, 40 g/l, 50 g/l, 60 g/l, 70 g/l, 80 g/l, 90 g/l, 100 g/l, 110 g/l, 120 g/l, 130 g/l, 140 g/l, 150 g/l, 175 g/l, 200 g/l, 225 g/l or 250 g/l octanoic acid per day.

The present inventors have determined that administering octanoic acid in the form of MCTs results in a rapid increase in plasma and brain ketone levels. The inventors have also determined that administering decanoic acid in the form of MCTs results prolonged increase in plasma and brain ketone levels. Without wishing to be bound by theory, the inventors consider that this may be because octanoic acid is more rapidly metabolised in vivo.

Thus, the composition may comprise decanoic acid and octanoic acid.

The composition may comprise an approximately equal ratio of decanoic acid and octanoic acid. In other words, the ratio of decanoic acid to octanoic acid may be approximately 1:1 wt/wt.

The composition may comprise a higher ratio of decanoic acid to octanoic acid. For example, the ratio of decanoic acid to octanoic acid may be approximately 2:1, 3:1, 4:1, 5:1 or 10:1 wt/wt.

In a particular embodiment, the ratio of decanoic acid to octanoic acid may be approximately 3:2 wt/wt.

The composition may be free from or substantially free from mono- or poly-unsaturated fatty acids.

The composition may have a ketogenic ratio of 0.2 to 0.3:1. In other embodiments, the ratio may be 0.5:1 or 1:1 to 5:1. "Ketogenic ratio" refers to the weight of lipid to the sum of weights of carbohydrate and protein.

The composition may be in the form of a tablet, dragees, capsule, gel cap, powder, granule, solution, emulsion, suspension, coated particle, spray-dried particle or pill.

The composition may be usable for reconstitution in water. The composition may be an oil-in-water emulsion.

The composition may be inserted or mixed into a food substance. The composition may be in the form of a food stuff, for example a human food stuff.

The composition may be in the form of a nutritional supplement. A nutritional supplement refers to a product which is intended to supplement the general diet of a subject.

The composition may be in the form of a complete nutritional product. A complete nutritional product refers to a product which is intended to be the sole item or meal or diet consumed by a subject.

The composition may be in the form of a beverage, mayonnaise, margarine, low fat spread, a dairy product, a cheese spread, processed cheese, a dairy dessert, a flavoured milk, cream, a fermented milk product, cheese, butter, a condensed milk product, an ice cream mix, a soya product, pasteurised liquid egg, a bakery product, a confectionary product, confectionary bar, chocolate bar, high fat bar, liquid emulsion, spray dried powder, freeze dried powder, HUT pudding, Pasteurised pudding, gel, jelly, yoghurt or a food with a fat-based or water-containing filling.

The composition may be an infant formula.

In general terms, administration of the composition may be by an oral route or another route into the gastro-intestinal tract, for example the administration may also be by gastric tube feeding.

The composition may be enriched with a MCFA. In particular, the composition may be enriched with octanoic acid and/or decanoic acid.

'Enriched' means that the MCFA has been added to the composition. For example, the MCFA may be spiked (i.e. added within or into) the composition.

In one embodiment, where a food or food extract natively contains a MCFA, enriched with a MCFA means that the enriched food or food extract comprises a greater amount of the MCFA than occurs natively in the food or food extract.

For example, an enriched composition, food or food extract may comprise at least 1.5-, at least 2-, at least 5-, at least 10-, at least 20-, at least 50- or at least 100-fold more MCFA than an equivalent native composition, food or food extract which has not been enriched.

The present invention also provides the use of a MCFA as defined herein in the manufacture of a composition for the treatment and/or prevention of anxiety.

In one aspect the invention relates to the use of a MCFA in the manufacture of a medicament for the treatment and/or prevention of anxiety The medicament may comprise one or more suitable pharmaceutically acceptable carriers excipients.

The present invention also provides a composition comprising a decanoic acid to octanoic acid ratio of about 3:2 wt/wt.

The decanoic acid and octanoic acid may be in the form of MCTs. The fatty acid moieties of the MCTs may comprise the same number of carbons.

A composition may be in a form defined herein.

Anxiety

Anxiety is an unpleasant state of inner turmoil, often accompanied by nervous behaviour, such as pacing back and forth, somatic complaints and rumination. It is the subjectively unpleasant feelings of dread over anticipated events and as such may be described as a feeling of fear, worry and uneasiness, usually generalized and unfocused as an overreaction to a situation that is only subjectively seen as menacing.

There are several recognised types of anxiety disorders, including panic disorder, social anxiety disorder, specific phobias and generalised anxiety disorder. Symptoms vary depending of the type of anxiety disorder, but generally include: feelings of panic, fear and uneasiness; problems sleeping; cold or sweaty hands and/or feet; shortness of breath; heart palpitations; dry mouth; numbness or tingling in the hands or feet; nausea; muscle tension and dizziness.

Anxiety is commonly tested via validated questionnaires. For example, The General Health Questionnaire consists of sixty questions about mild somatic and anxiety symptoms. Thirty- and 12-item questionnaires are also commonly used. The Patient Health Questionnaire (PHQ-9) and the Center for Epidemiologic Studies Depression Scale (CES-D) as further examples of anxiety scales.

Clinicians usually diagnose anxiety via short interviews, asking about specific anxiety-generating environments and responses. These are used to classify anxiety into subtypes such as social anxiety, general anxiety disorder, panic disorder or phobic disorder.

The anxiety may be stranger anxiety, social anxiety disorder, generalised anxiety disorder, general anxiety, phobia, panic disorder, obsessive-compulsive disorder or posttraumatic stress disorder.

Stranger anxiety is a form of distress that children experience when exposed to people unfamiliar to them. Symptoms may include: getting quiet and staring at the stranger, verbally protesting by cries or other vocalizations, and hiding behind a parent.

Social anxiety disorder is a persistent fear about social situations and being around people. It is one of the most common anxiety disorders.

Generalised anxiety disorder (GAD) is an anxiety disorder that is characterized by excessive, uncontrollable and often irrational worry/apprehensive expectation about events or activities. Individuals often exhibit a variety of physical symptoms, including fatigue, fidgeting, headaches, nausea, numbness in hands and feet, muscle tension, muscle aches, difficulty swallowing, bouts of difficulty breathing, difficulty concentrating, trembling, twitching, irritability, agitation, sweating, restlessness, insomnia, hot flashes, and rashes and inability to fully control the anxiety.

The Diagnostic and Statistical Manual of Mental Disorders (2013) defines GAD by the following criteria:

A. Excessive anxiety and worry (apprehensive expectation), occurring more days than not for at least 6 months, about a number of events or activities (such as work or school performance).
B. The individual finds it difficult to control the worry.
C. The anxiety and worry are associated with three (or more) of the following six symptoms (with at least some symptoms having been present for more days than not for the past 6 months):
Restlessness or feeling keyed up or on edge.
Being easily fatigued.
Difficulty concentrating or mind going blank.
Irritability.
Muscle tension.
Sleep disturbance (difficulty falling or staying asleep, or restless, unsatisfying sleep).
D. The anxiety, worry, or physical symptoms cause clinically significant distress or impairment in social, occupational, or other important areas of functioning.
E. The disturbance is not attributable to the physiological effects of a substance (e.g., a drug of abuse, a medication) or another medical condition (e.g., hyperthyroidism).
F. The disturbance is not better explained by another mental disorder (e.g., anxiety or worry about having panic attacks in panic disorder, negative evaluation in social anxiety disorder social phobia, contamination or other obsessions in obsessive-compulsive disorder, separation from attachment figures in separation anxiety disorder, reminders of traumatic events in posttraumatic stress disorder, gaining weight in anorexia nervosa, physical complaints in somatic symptom disorder, perceived appearance flaws in body dysmorphic disorder, having a serious illness in illness anxiety disorder, or the content of delusional beliefs in schizophrenia or delusional disorder).

Phobia (phobic anxiety) includes all cases in which fear and anxiety is triggered by a specific stimulus or situation. Sufferers typically anticipate terrifying consequences from encountering the object of their fear, which can be anything from an animal to a location to a bodily fluid to a particular situation.

Panic disorder is when a person suffers from brief attacks of intense terror and apprehension, often marked by trembling, shaking, confusion, dizziness, nausea, and/or difficulty breathing. These panic attacks arise abruptly and peak in less than ten minutes, although they can last for several hours. Attacks can be triggered by stress, fear, or even exercise; the specific cause is not always apparent.

Obsessive-compulsive disorder is an anxiety disorder characterized by intrusive thoughts that produce uneasiness, apprehension, fear or worry (obsessions), repetitive behaviours aimed at reducing the associated anxiety (compulsions), or a combination of such obsessions and compulsions.

Posttraumatic stress disorder may develop after a person is exposed to one or more traumatic events, such as sexual assault, warfare, serious injury, or threats of imminent death. The diagnosis may be given when a group of symptoms, such as disturbing recurring flashbacks, avoidance or numbing of memories of the event, and hyperarousal, continue for more than a month after the occurrence of a traumatic event.

The anxiety treated and/or prevented according to the present invention is not associated with age-related cognitive decline.

Treating and/or Preventing

To "treat" means to administer a MCFA or composition as described herein to a subject having existing anxiety in order to lessen, reduce or improve at least one symptom associated with the anxiety and/or to slow down, reduce or block the progression of the anxiety.

To "prevent" means to administer a MCFA or composition as described herein to a subject is not showing any symptoms of to reduce or prevent development of at least one symptom associated with the anxiety.

Symptoms of anxiety may be determined using questionnaires and interviews as described above.

Subject

The subject may be, but is not limited to, mammals such as bovine, canine, caprine, cervine, equine, feline, human, ovine, porcine and primates. Preferably the subject is a human.

The subject may be a child or an infant.

In various embodiments, the subject may have, or be suspected of or at risk of, anxiety.

The invention will now be further described by way of Examples, which are meant to serve to assist one of ordinary skill in the art in carrying out the invention and are not intended in any way to limit the scope of the invention.

EXAMPLES

Example 1

MCTs Reduce Levels of Anxiety

Figure 1:
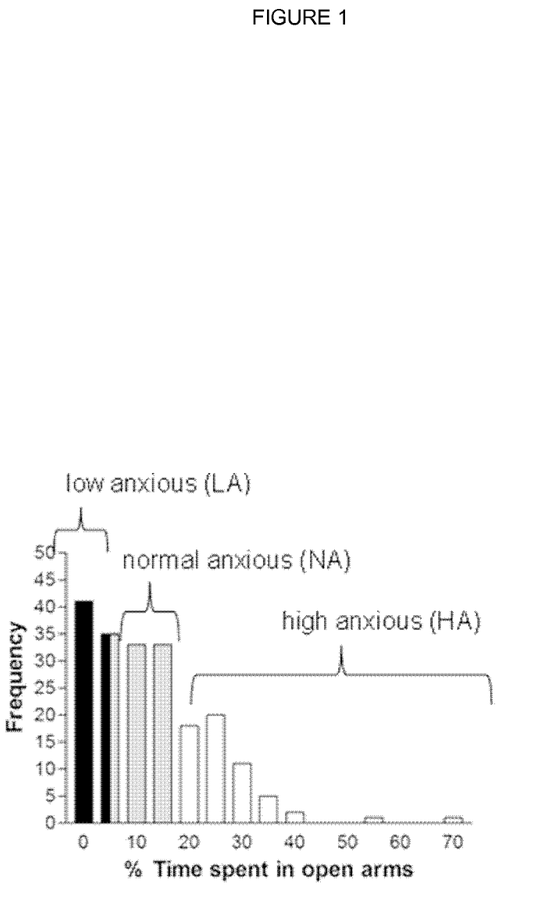
FIG. 1—Elevated plus maze: percentage time spent in open arms. Rats were divided in tertiles of anxiety levels: high anxiety, HA; normal anxiety, NA; low anxiety, LA.

One hundred rats were phenotyped for innate anxiety via the elevated plus maze and separated into 3 groups: high anxiety (HA), normal anxiety (NA) and low anxiety (LA) (see FIG. 1).

Figure 2:
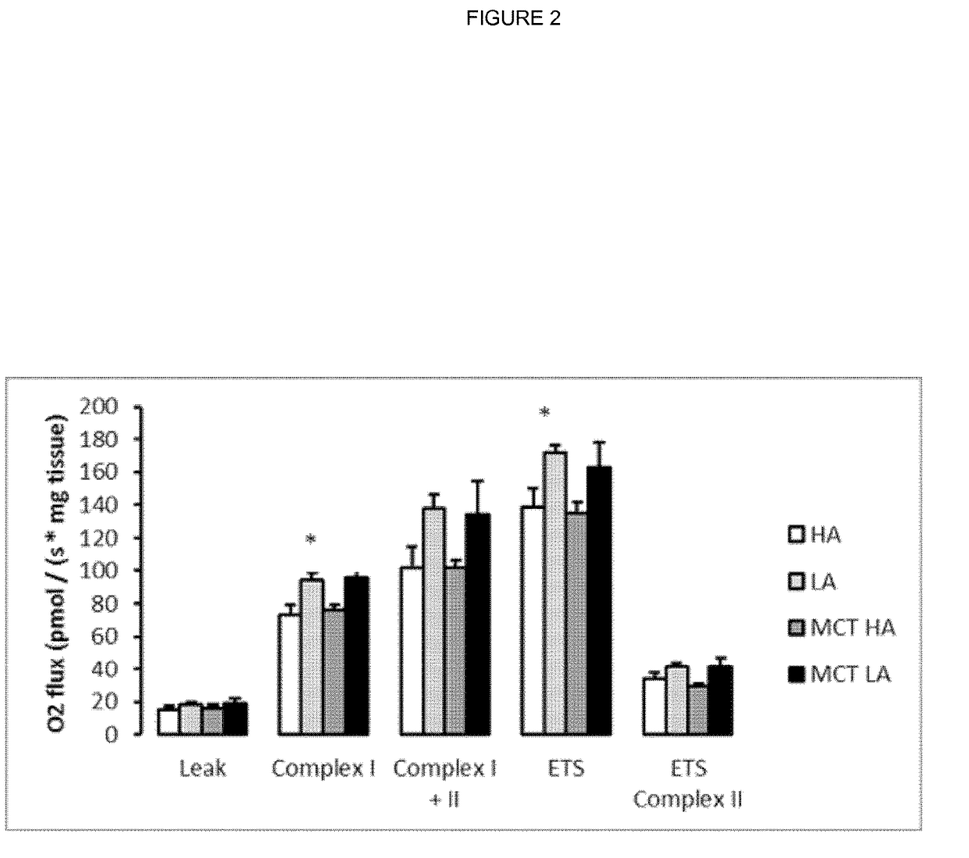
FIG. 2—Oxygen consumption of nucleus accumbens homogenate in MCT vs control-treated rats divided into tertiles of innate anxiety, high anxiety, HA; normal anxiety, NA; low anxiety; LA; *, $p<0.05$ LA compared to HA FIG. 3A—Light dark box: Percentage time spent in the light compartment in control vs MCT-treated rats*, $p<0.05$.
Figure 3A:
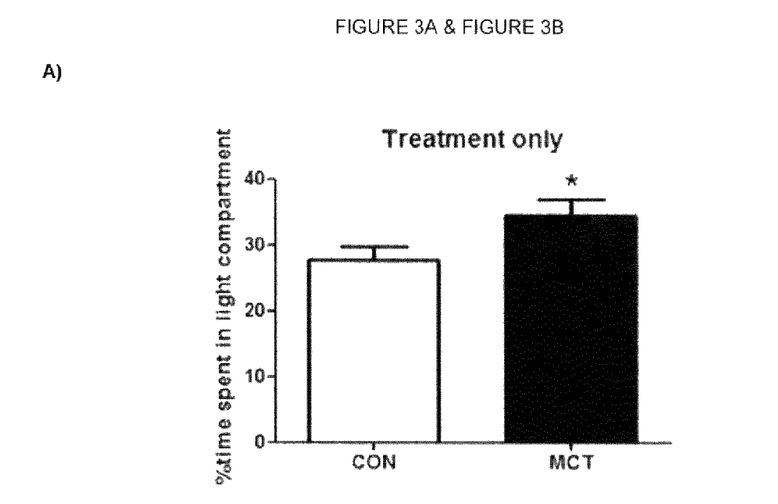
Figure 3B:
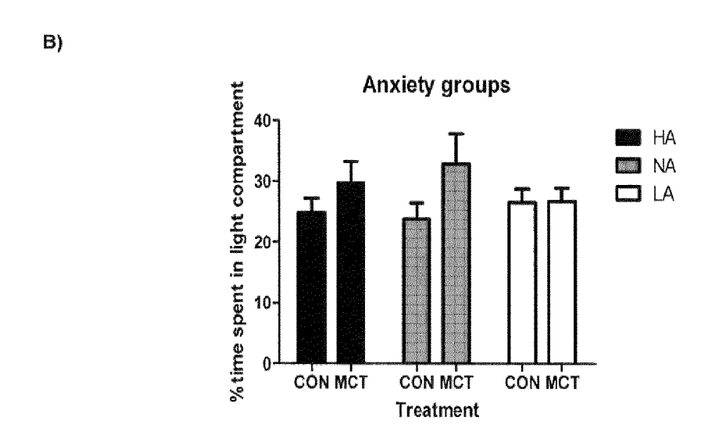
FIG. 3B—Light-dark box: Percentage time spent in the light compartment in control vs MCT treated rats were divided in tertiles of innate anxiety levels, high anxiety, HA; normal anxiety; NA; low anxiety, LA.

MCTs (C8:C10) had no effect on nucleus accumbens oxygen consumption compared to control diet, while strong differences were seen between the anxiety phenotypes (HA vs LA) (see FIG. 2).

Two weeks of MCTs improved anxiety levels in unstressed rats, mainly in the low anxiety group.

Figure 4A:
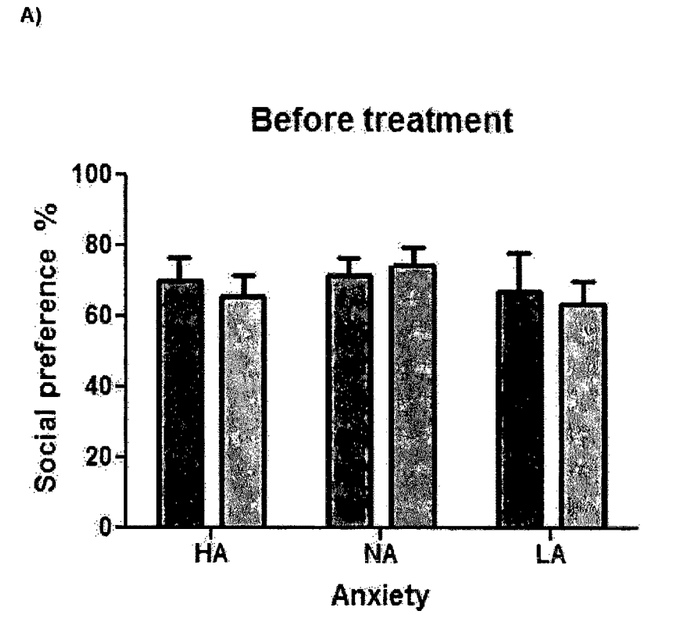
FIG. 4—A) Social preference test before MOT or control treatment where rats are divided into tertiles of innate anxiety: high anxiety, HA; normal anxiety, NA; low anxiety, LA; Percentage time spent in the compartment containing juvenile rat; AB) Social preference test after treatment. control vs MCT-treated *, p<0.05
Figure 4B:
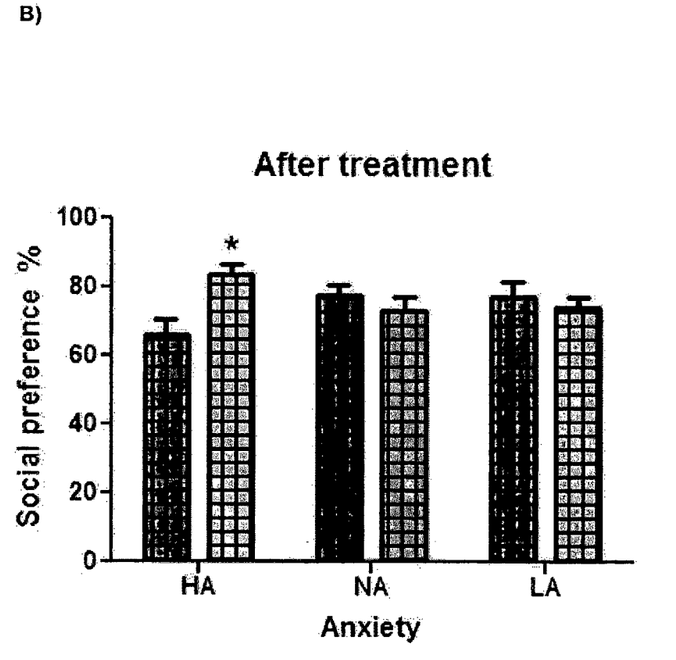

Social interaction was improved by MCTs in the high anxiety group (see FIG. 4).

Figure 5A:
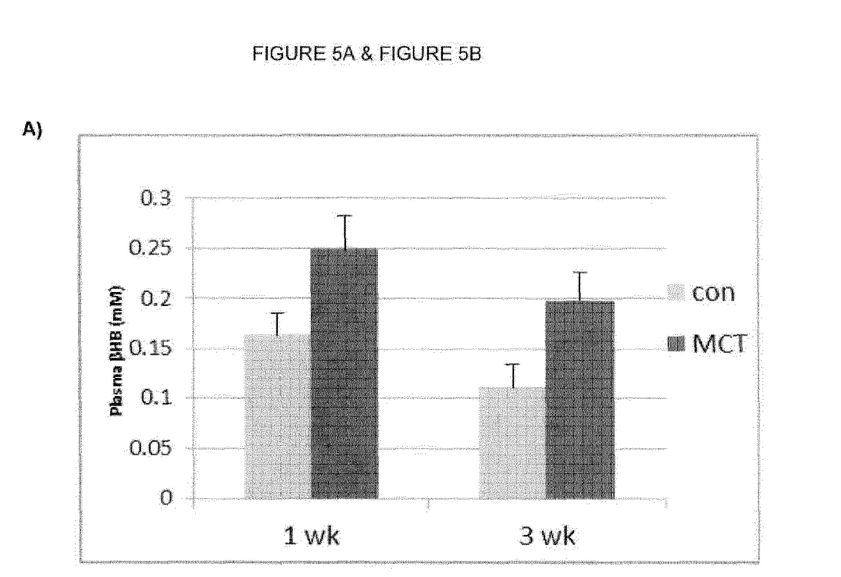
FIG. 5—A) Plasma BHB at 1 and 3 weeks in control vs MCT-treated rats; B) Brain BHB at 3 weeks in control vs MCT-treated rats. The plasma was measured for beta-hydroxybuyrate (BHB) at 7 days after treatment and at sacrifice. BHB where at both 1 and 3 weeks BHB was significantly increased, as were brain BHB at 3 weeks (P≤0.05).
Figure 5B:
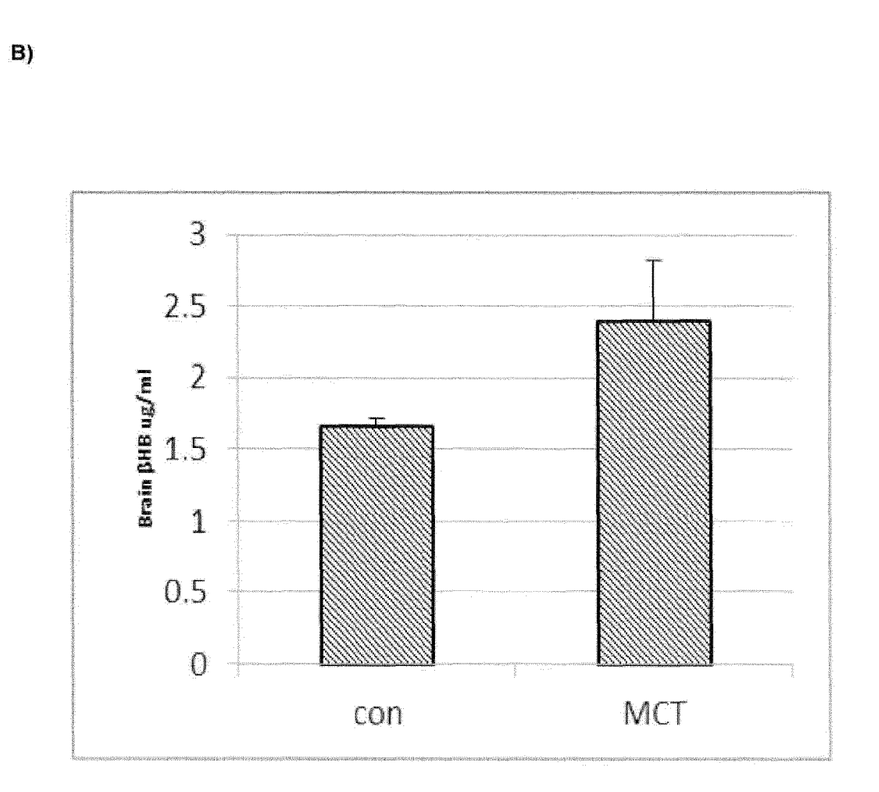
Figure 6:
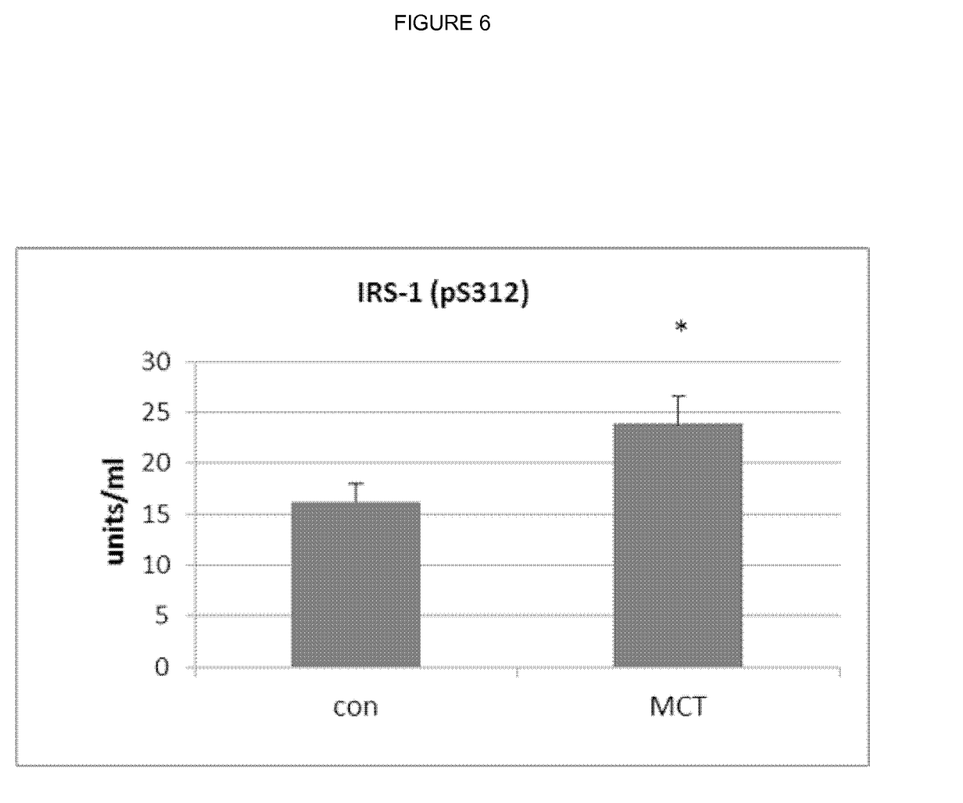

Ketone levels were slightly raised at 1 and 3 weeks after the intervention (see FIG. 5) and IRS-1 phosphorylation in striatum homogenate was also increased following MCT intervention (see FIG. 6).

These results suggest that innate anxiety is directly linked to mitochondrial function. In particular, the results indicate that short term administration of MCTs alleviates anxiety, possibly via an IRS-1 pathway.

Figure 7:
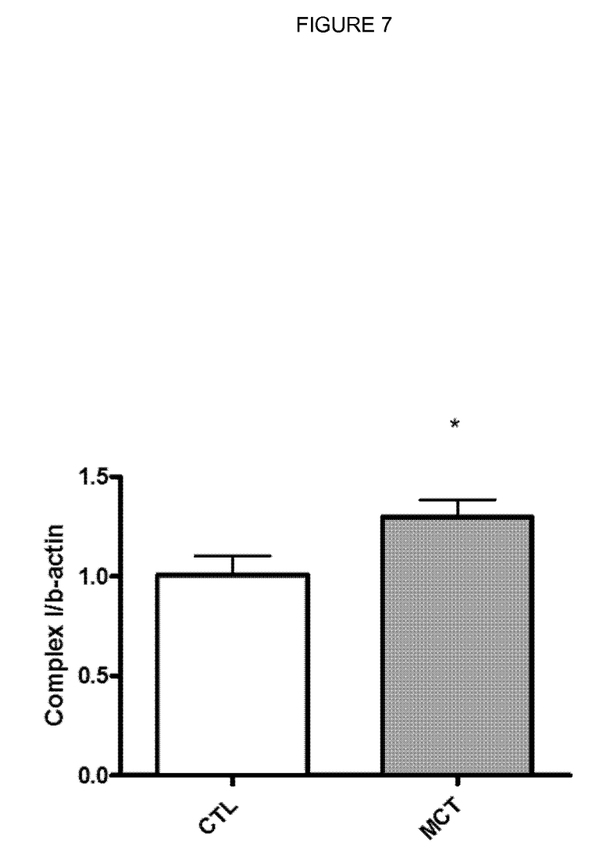

Complex 1 protein expression was increased in rat cortex following a two-week period of MCT ingestion (see FIG. 7).

Example 2

Figure 8A:
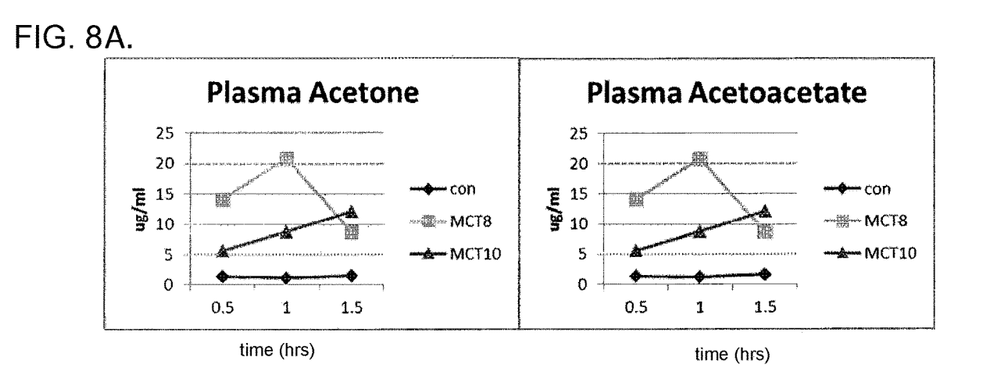

Differing Temporal Dynamics of Plasma and Brain Ketone Levels Following Octanoic Acid or Decanoic Acid Administration Plasma ketone levels increased more rapidly after octanoic acid ingestion compared to deconaoic acid ingestion (see FIG. 8A).

Figure 8B:
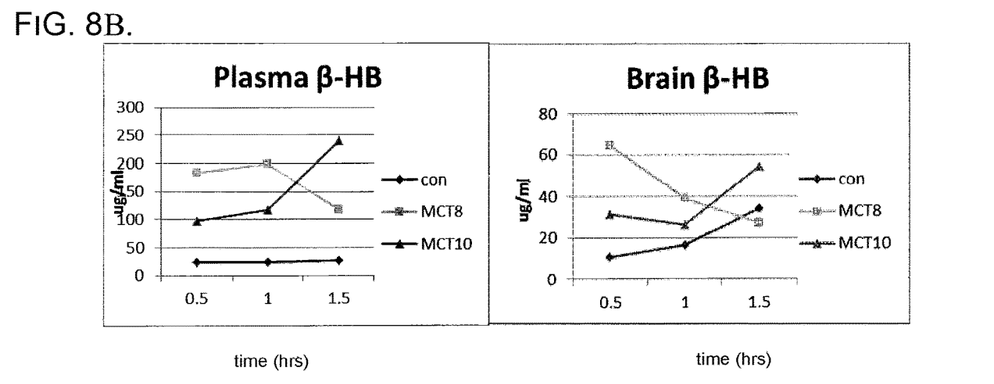

Plasma $\beta$-HB showed similar kinetics to brain $\beta$-HB, with ingestion of octanoic acid causing a more rapid increase and ingestion of decanoic acid providing a longer-lasting increase (see FIG. 8B).

Methods

Animal Phenotyping and Diet Intervention

One hundred male Wistar rats were housed individually in standard rat cages enriched with a cardboard tube and tissue and ad libitum food and water. After acclimatization of 1 week all rats were weighed, then tested for baseline anxiety using the elevated plus maze test.

The elevated plus maze (EPM) apparatus consists of four arms, two are open while others are closed on the sides and at the end. Each arm has a length of 50 cm. On the test day, the rat was placed on the centre of the maze at a low level of lighting (15 lux on the open arms and 5 lux in the closed) and its behaviour was observed for 5 min. The parameters evaluated include: the time spent by rats in the open arms in the closed arms and in the central part of the maze. Various behaviors such as grooming, immobility and stretch-attend postures were also measured.

Three days following the EPM animals were given a social interaction test. The animals were habituated to placement into a novel cage for thirty minutes for three days prior to the testing session. On the day of the test, animals were weight-matched, paired into dyads, placed into a novel cage and allowed to fully interact for thirty minutes, during which time their behaviour was video recorded.

Rats were separated into 3 groups according to anxiety: high, normal and low. High, normal and low anxiety rats were further subdivided into feeding groups. Sixteen each of high, normal and low anxiety rats were given a diet of 5% medium chain triglycerides (40:60 of octanoic acid triglyceride and decanoic triglyceride) and fifteen each were given control diet (5% sunflower oil) via specially formulated animal chow for 15 days. The diet was in the form of animal chow with normal fat, carbohydrate and protein ratios as standard chow diets. Following one week exposure of experimental diet, animals were evaluated for emotional behaviour using the following sequence of tests with two day intervals of rest in between: light-dark box test, social interaction test, and social dominance test. Rats were weighed every week to ensure weight maintenance. After 15 days the rats were sacrificed by decapitation and brains collected for RNA and protein analyses.

Light-dark Box Test

The light dark box is composed of a three-chambered apparatus in the shape of a long rectangle. One chamber is light with a solid floor. Another is dark, with a grid floor. These two chambers are separated by a middle chamber that is smaller and grey. Animals were placed in the middle chamber and allowed to acclimate. Following acclimation, they were allowed to freely explore the other two chambers for 5 minutes. The amount of time that the animal spent in the light and dark chambers and the number of entries was recorded. This test offers the possibility to measure the degree of trait anxiety in the animals. Animals that are "anxious" spend less time in the light chamber and make fewer entries into that chamber.

Social Interaction Test

Animals were placed into a three-chambered apparatus and given the choice between investigating an object or a contained juvenile for 10 minutes. The juveniles were between the ages of PND25-32 to avoid eliciting any aggression from the experimental animal. Juveniles were habituated to the apparatus and the chamber one day prior to testing to reduce their stress and anxiety levels. During the experiment, subjects were placed in the middle chamber without access to the other two chambers to habituate to the environment for 5 minutes. The doors were then removed and animals were allowed free access to the two chambers for 10 minutes. The time spent investigating the juvenile compared to the object was recorded and scored by an observer blind to the treatment and converted to a percentage. Animals were designated as having a social preference when this time exceeds 50%. Animals were then returned to their home cage for 30 minutes. Following this intertrial interval, animals were returned to the apparatus. This time, instead of an object, a new juvenile was placed in the chamber. The animal was placed in the central chamber and given the option to explore a novel juvenile (in place of the object) or the juvenile from the last trial. Animals with a strong social memory spent more time exploring the novel juvenile over the 5 minute course of the test.

Plasma and Brain Ketones

Blood was drawn from the tail vein 7 days after initiation of treatment and trunk blood was collected during sacrifice. Blood was centrifuged and plasma samples were analysed for beta-hydroxybutyrate using a colorimetric kit (Cayman, US). For measurement of brain ketones, sample preparation involved liquid/liquid extraction of 50 µl brain tissue supernatant (pH 2), and extract derivatization with MSTFA (silylation). Analysis of BHB was performed via GC/MS, int. Standard 13C2-3-OH-But, m/z 233 (3-OH-But), m/z 118 (13C2-3-OH-But), with a calibration of 2-24 µg/ml (water); LOQ: 2 µg/ml, LOD: 0.7 µg/ml.

Western Blot

Tissues were homogenized in 200 mL Tris buffer (pH 7.4) containing 10% sucrose and protease inhibitors sonicated, and kept at −80° C. until use. Protein amounts were evaluated using the BCA assay diluted and then separated on gels. Proteins were transferred to nitrocellulose membranes, which were then saturated (5% BSA) and incubated with primary (rabbit PSD-95) and secondary antibodies.

ELISA

Protein extracts were prepared from homogenates of striatum tissue. Kits containing antibodies to IRS-1 and phosphorylated IRS-1 (pS312) (Life Technologies) were used to probe total protein content vs phosphorylated protein via sandwich ELISA.

Studying Temporal Dynamics of Octanoic Acid and Deconoic Acid Ingestion

Control rats received oral gavage of sunflower oil, as described above. MCT8 and MCT10 received oral gavage of octanoic acid or decanoic acid, respectively. Rats were sacrificed and trunk blood, portal vein blood and brain, pancreas and liver were collected as indicated.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cell biology or related fields are intended to be within the scope of the following claims.

The invention claimed is:

1. A composition for treating anxiety, the composition comprising a daily dosage of 5 g/l to 250 g/l of a medium chain fatty acid (MCFA) effective for treating the anxiety, wherein the MCFA comprises deconoic acid and octanoic acid in a ratio of 1:1 to 2:1 wt/wt or 4:1 to 10:1 wt/wt.

2. The composition according to claim 1, wherein the deconoic acid and the octanoic acid are present in a ratio of 3:2 wt/wt.

3. The composition according to claim 1, wherein the composition further comprises a food substance.

4. The composition according to claim 1, wherein the anxiety is selected from the group consisting of stranger anxiety, social anxiety disorder, generalized anxiety disorder, general anxiety, phobia, panic disorder, obsessive-compulsive disorder, posttraumatic stress disorder, and combinations thereof.

* * * * *